(12) United States Patent
Chen

(10) Patent No.: US 7,039,456 B2
(45) Date of Patent: May 2, 2006

(54) CONDUCTANCE PATH MECHANISM FOR WIRELESS HEARTBEAT TRANSMITTER

(76) Inventor: Shui Jung Chen, No. 88-7, Kwang Fu Rd., Sec. 1., San Chung City, Taipei Hsien (TW)

( * ) Notice: Subject to any disclaimer, the term of this patent is extended or adjusted under 35 U.S.C. 154(b) by 497 days.

(21) Appl. No.: 10/354,962

(22) Filed: Jan. 31, 2003

(65) Prior Publication Data

US 2004/0171951 A1 Sep. 2, 2004

(51) Int. Cl.
*A61B 5/04* (2006.01)
(52) U.S. Cl. .................. 600/509; 439/909; 600/386
(58) Field of Classification Search ............... 600/509, 600/386; 439/909; 607/37
See application file for complete search history.

(56) References Cited

U.S. PATENT DOCUMENTS

| | | | |
|---|---|---|---|
| 4,952,928 A | 8/1990 | Carroll et al. | |
| 5,353,793 A | 10/1994 | Bornn | |
| 5,628,324 A | 5/1997 | Sarbach | |
| 5,778,880 A * | 7/1998 | Chen | 600/509 |
| 5,956,661 A | 9/1999 | Lefebvre et al. | |
| 6,229,454 B1 | 5/2001 | Heikkila et al. | |
| 6,289,238 B1 * | 9/2001 | Besson et al. | 600/509 |

FOREIGN PATENT DOCUMENTS

| | | |
|---|---|---|
| GB | 2257523 | 1/1993 |
| WO | WO88/09146 | 12/1988 |

\* cited by examiner

*Primary Examiner*—Mark Bockelman
*Assistant Examiner*—Eric Bertram
(74) *Attorney, Agent, or Firm*—Bacon & Thomas, PLLC

(57) ABSTRACT

This invention relates to a conductance path mechanism of a wireless heartbeat transmitter comprising a circuit board, a spiral spring, a U-shaped contact rod integrally molded to both side of a bottom cover and a rubber conductible sheet. A horizontal portion of said U-shaped contact rod is totally inserted inside a foundation of a bottom cover to form a steady mechanism of the present invention.

4 Claims, 3 Drawing Sheets

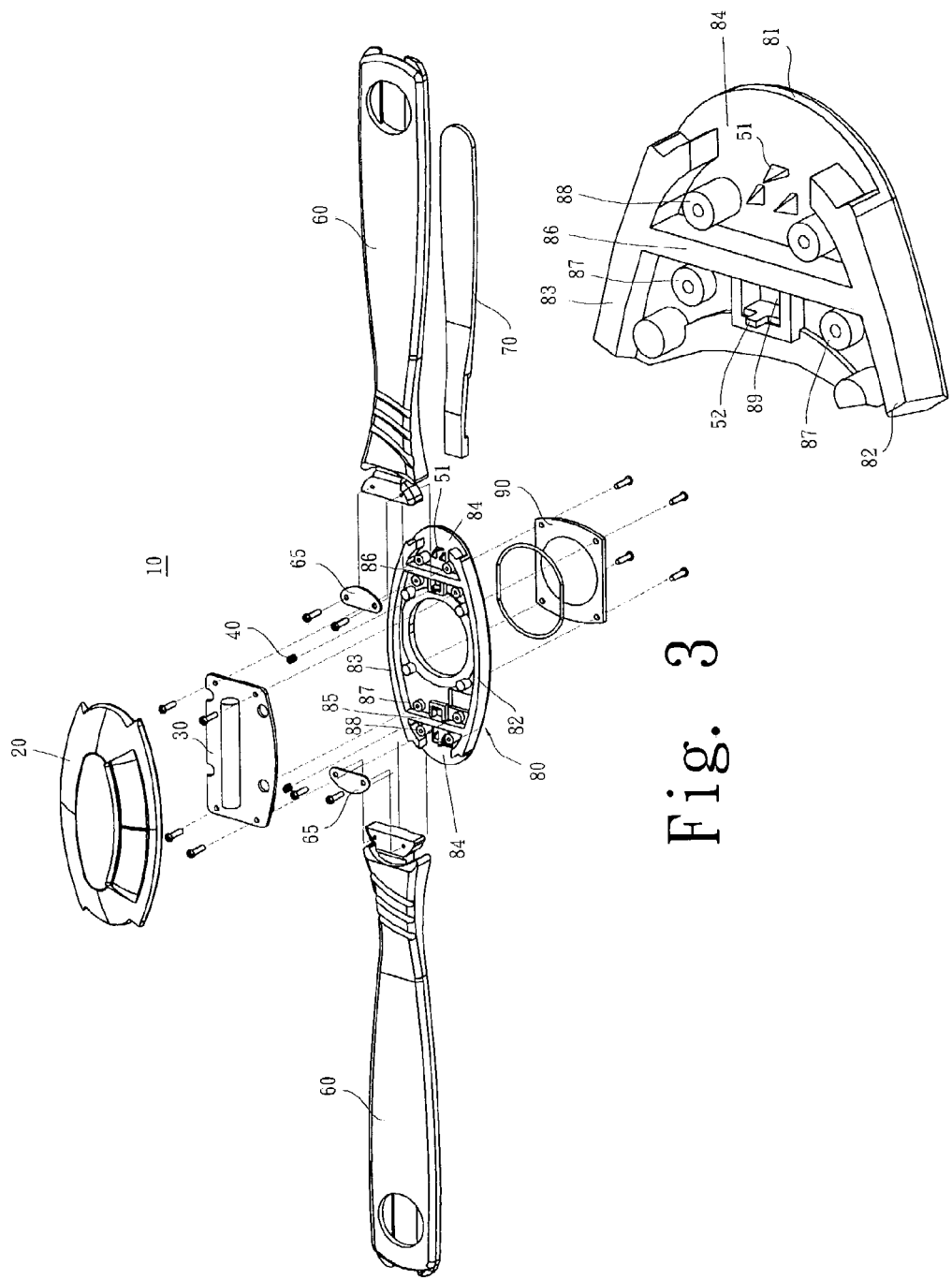

CONDUCTANCE PATH MECHANISM FOR WIRELESS HEARTBEAT TRANSMITTER

BACKGROUND OF THE INVENTION

1. Field of the Present Invention

The present invention relates to conductance path mechanism for a wireless heartbeat transmitter; and more particularly, relates to the bottom cover mechanism of a wireless heartbeat transmitter with an U-shaped contact rod integrally molded which U-shaped contact rod is provided with three upward vertical pins inserted into a rubber conductible sheet to make an excellent insert-connection of electricity conductance to wireless heartbeat transmitter.

2. Description of Prior Art

The prior wireless heartbeat transmitter includes a conductible rubber used as an electrode for monitoring heartbeat signal, and a circuit board with a signal transmitter. While the conductible rubber and the circuit board form an electrical connection, the heartbeat signal monitored by the conductible rubber is wirelessly transmitted from the signal transmitter of the circuit board to a separate but corresponding receiver to reach a goal of wirelessly monitoring an user's heartbeat.

The key point of the prior wireless heartbeat transmitter regarding its quality and accuracy to heartbeat signal is that whether the electrical connection between the conductible rubber and the circuit board is good or not, which means that the structure of electrical connection or conductance path between the conductible rubber and the circuit board needs to be durable and steady enough to endure the disturbance of vibration and to refrain from dirt, damp, and wearing to transmit accurate and distortionless monitored heartbeat signal.

Therefore, how to develop a superior electrical connection and conductance path between rubber conductible and circuit board to transmit accurate and distortionless monitored heartbeat signal is the main purpose for designer who wants to make an improvement to the prior wireless heartbeat transmitter.

The structures of prior wireless heartbeat transmitters used to build an electrical connection or conductivity path between the circuit board and the conductible rubber is shown as FIG. 1, which structure is to attach the bottom of the rubber conductible sheet (4) at front section to the top surface of a metal plate (23) and to install a bent spring sheet (11) at each side of the bottom of the circuit board (1); the rubber conductible sheet (4) and the circuit board (1) becomes connected state by the attachment of the bottom of said spring sheet (11) to the top surface of said metal plate (23). This kind of conductivity path structure is vulnerable to dirt, damp, and wearing, and the spring sheet (11) is easy to suffer mal-contact caused by vibration since said rubber conductible sheet (4) and said metal plate (23) are only "surface to surface" contact, which makes the lack of accuracy of the heartbeat signal monitored by the rubber conductible sheet (4).

The conductance structure of the aforementioned prior art is an unstable and poor electrical contact, due to only "surface to surface" contact between rubber conductible plate (50) and circuit board (30), which causes defects of distorted signal.

SUMMARY OF THE PRESENT INVENTION

The primary purpose of the present invention is to provide a novel conductance structure to wireless heartbeat transmitter having a conductance path mechanism comprising a rubber conductible sheet, an U-shaped contact rod, a spiral spring, and a circuit board, wherein the horizontal portion of said U-shaped contact rod is totally inserted inside a foundation of a bottom cover to form a steady mechanism; and, one vertical end of said U-shaped contact rod forms three upward vertical pins which are inserted into a rubber conductible sheet.

The secondary purpose of the present invention is to make the rubber conductible sheet with a steady conductible contact mechanism due to insert-connection, which mechanism is steady enough to endure the disturbance of vibration to improve the defects of prior art only with "surface to surface" contact to cause distortion of monitored signal.

The third purpose of the present invention is to provide a wireless heartbeat transmitter, of which the other vertical end of said U-shaped contact rod forms a contact positioning pin which makes a spiral spring collar a contact positioning pin to make a superior electrical contact formed by said circuit board and said U-shaped contact rod and make a steady conductance path mechanism formed by said circuit board conductible sheet, said U-shaped contact rod, said spiral spring, and said circuit board as a whole.

The other purpose of the present invention is to provide a wireless heartbeat transmitter which uses said bottom cover and said U-shaped contact rod to form an integrally molded mechanism to reach an effect of water proof and uses a separating plate rib and a detent rib bulging from said foundation of said bottom cover, coordinated with an upper cover and fixing bands, to form a wireless heartbeat transmitter having a steady and firm electrical connection mechanism which owning effect of water and mist proof.

BRIEF DESCRIPTION OF THE DRAWING FIGURES

FIG. 3 is an explosion drawing of the wireless heartbeat transmitter of the present invention.

FIG. 4 is a locally enlarged drawing of said bottom cover (80).

DETAILED DESCRIPTION OF THE PREFERRED EMBODIMENTS

Figure 1:
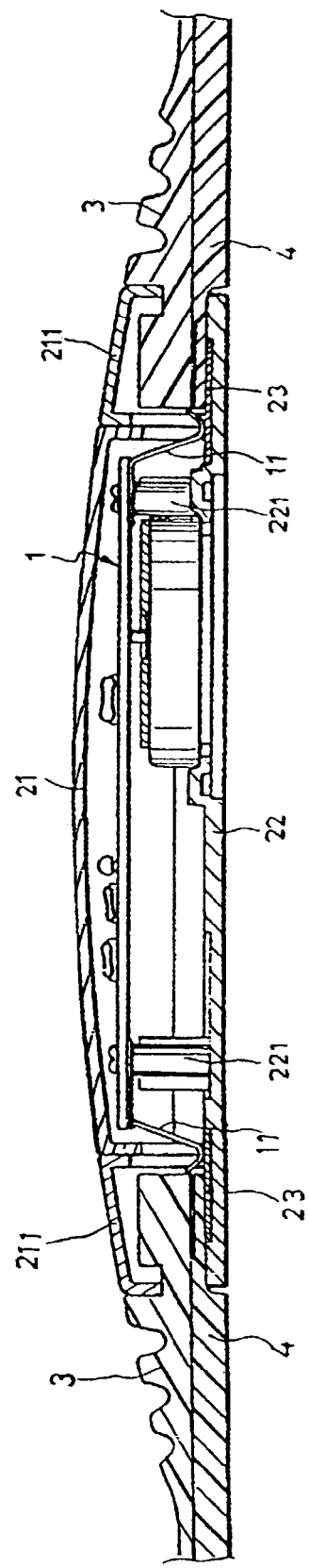
FIG. 1 is a mechanism of the prior wireless heartbeat transmitter.
Figure 2:
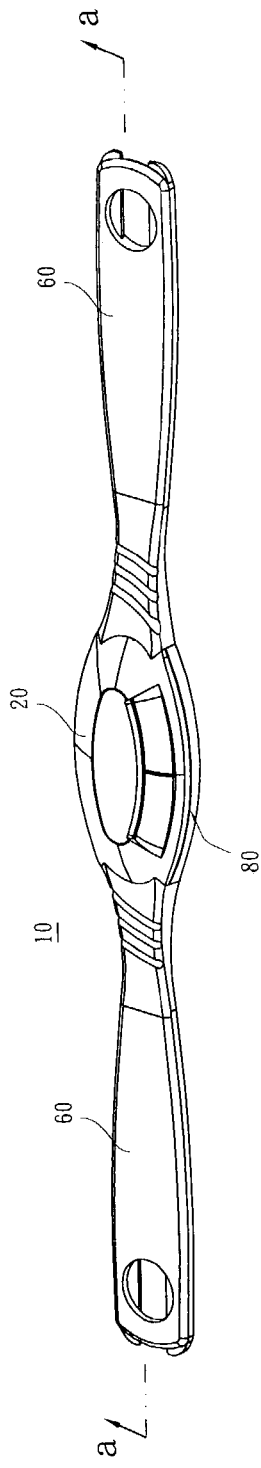
FIG. 2 is a perspective drawing of the wireless heartbeat transmitter of the present invention.
Figure 6:
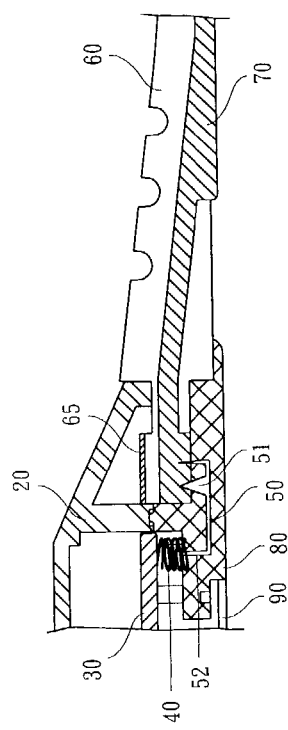
FIG. 6 is a locally enlarged drawing of "A" district of FIG. 5.
Figure 5:
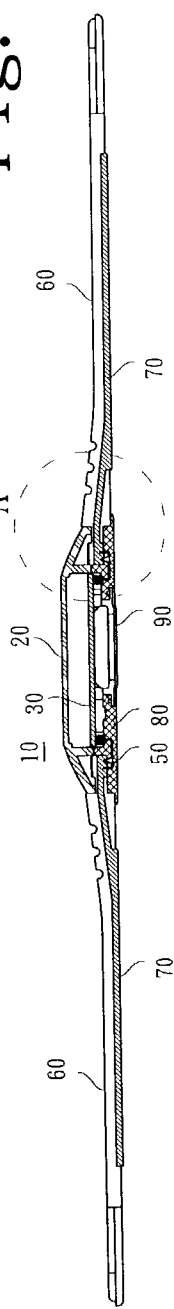
FIG. 5 is a cross-section drawing of FIG. 2 along a—a line.

Referring to from FIG. 2 to FIG. 6, the wireless heartbeat transmitter (10) of the present invention comprises an upper cover (20), a bottom cover (80), a circuit board (30), two spiral springs (40), two U-shaped contact rods (50) integrally molded to both left and right sides of said bottom cover (80), two fixing bands (60), two rubber conductible sheets (70), two pressing plate (65), and a battery cover (90).

The mechanism of said bottom cover (80), which is the key portion for the present invention to reach tight electrical connection and superior conductance path, has a foundation (81) forming the base of said bottom cover (80), a front wall rib (82) and a rear wall rib (83) symmetrically forming both side end walls of said bottom cover (80) and making both side ends of said bottom cover (80) form an opening (84), and a left wall rib (85) and a right wall rib (86) located at an appropriate location close to both ends of said front wall rib (82) and said rear wall rib (83); therefore, said bottom cover is made to have three districts comprising: a central district circled by said foundation (81), said front wall rib (82), said rear wall rib (83), said left wall rib (85), and said right wall rib (86); a left district located at the left side of said left wall rib (85) and having an opening (84); a right district located at the right side of said right wall rib (86) and having an opening (84).

Said central district of said bottom cover (80) accommodates and fixes said circuit board (30), the central portion of said foundation (81) of said bottom cover (80) having a hole to accommodate a battery, and the four corners of the central district of said bottom cover (80) each having a hub rib (87) bulging from said foundation (81) respectively, said circuit board (30) being installed to said four hub ribs (67) with screws; therefore, while a battery is installed (not shown in drawing) and said battery cover (90) is covering said bottom cover (80), the battery provides the power needed by said circuit board (30). Said left district located at the left side of said left wall rib (85) and said right district located at the right side of said right wall rib (86) are utilized to fix and lock said fixing bands (60) at both left and right sides, so a hub rib (88) bulging from said foundation (81) respectively at the corners of said left district and said right district, said fixing band (60) collaring said hub rib (88), and said metal pressing plate (65) being fixed and locked with screws.

An U-shaped contact rod (50) is integrally molded to said foundation (81) at the neighboring area between said central district and said left district and at the neighboring area between said central district and said right district respectively, wherein the horizontal portion of said U-shaped contact rod (50) is totally inserted inside said foundation (81) of said bottom cover (80) to form a water-proof mechanism; each of both vertical ends of said two U-shaped contact rods (50) forms three upward vertical pins (51) which protrude into the left district and the right district of said bottom cover (80), and each of the other two vertical ends of said two U-shaped contact rods (50) forms a contact positioning pin (52) which protrudes into the central district of said bottom cover (80). In addition, two rib walls each respectively bulges at the surrounding area of said contact positioning pin at both sides of the central district of said bottom cover (80), each of which respectively forms a spring detent groove (89) with said left wall rib (85) and said right wall rib (86); however, the height of said contact positioning pin (52) is higher than that of said spring detent groove (89).

The positive electrode and the negative electrode at the bottom of said circuit board (30) are welded to said spiral springs (40); each of said spiral springs (40) at both sides of the bottom of said circuit board (30) respectively collars said contact positioning pins (52) of said two U-shaped contact rod (50), and the lower section of said spiral spring (40) is tightly inserted inside said spring detent groove (89) of said bottom cover (80) to make said spiral spring (40) and said contact positioning pin (52) form a good electrical contact and to make said spiral spring (40) and said bottom cover form a tight and steady mechanism; consequently, said circuit board (30) and said U-shaped contact rod (50) form a good electrical connect as well.

The bottom surface of said fixing band (60) is installed with a rubber conductible sheet (70) used for monitoring heartbeat signal; while the front ends of said fixing bands (60) are respectively locked inside the left district and the right district of said bottom cover (80), said three vertically upward pins (51) of said U-shaped contact rod (50) insert into the interior of said rubber conductible sheet (70), which makes an insert-connect type of conductible contact between said U-shaped contact rod (50) and said rubber conductible sheet (70). Due to that said pressing plate (65) is installed at the front end top surface of said fixing band (60), the pressing plate (65) presses said rubber conductible sheet (70) moving downward by means of tightly screwing itself to said hub rib (88) with a screw; meanwhile, the pins (51) of said U-shaped contact rod (50) are totally inserted into said rubber conductible sheet (70). Consequently, said rubber conductible sheet (70) has a good electrical connect with said U-shaped contact rod (50), and said rubber conductible sheet (70) owning its soft tight packing characteristic forms a tight pressing contact with the foundation (81) of said bottom cover (80), which prevents said pins (51) of said U-shaped contact rod (50) from contacting with air or water so as to make the pins (51) of said U-shaped contact rod (50) completely refrain from gasification, the signal thereby being kept distortionless; in addition, since the front end top surface of said fixing band (60) is locked and fixed by said pressing plate (65), the front end (81) of said fixing band (60) and the foundation of said bottom cover (80) form a tight and steady mechanism which will not loose at all while being used.

So, the aforementioned rubber conductible sheet (70), U-shaped contact rod (50), spiral spring (40), and circuit board (30) form a superior steady conductance path mechanism of the present invention; particularly, said bottom cover (80) and said U-shaped contact rod (50) form an integrally molded mechanism which further forms a tightly assembled wireless heartbeat transmitter (10) with said upper cover (20) and said fixing band (60). The wireless heartbeat transmitter has a mechanism of water and mist proof and a mechanism of steady electrical connect, which effectively improves the defects of prior wireless heartbeat transmitter.

In other words, the present invention has advantages listed as follows:

1. The U-shaped contact rod (50) is integrally molded to said bottom cover (80), and the horizontal portion of said U-shaped contact rod (50) is totally inserted into the interior of said bottom cover (80); each of both vertical ends of said two U-shaped contact rods (50) protrudes to expose; this mechanism makes said U-shaped contact rod (50) and said bottom cover (80) form a tight and steady structure which has superior water proof characteristic and will not be disturbed by vibration.

2. By using said pressing plate (65) and screw, said rubber conductible sheet (70) is totally inserted by the pins (51) of said U-shaped contact rod (50). Consequently, said rubber conductible sheet (70) has a good electrical connect with said U-shaped contact rod (50), and said rubber conductible sheet (70) owning its soft tight packing characteristic wraps the pins (51) completely, which prevents said pins (51) of said U-shaped contact rod (50) from contacting with air or water so as to make the pins (51) of said U-shaped contact rod (50) completely refrain from corrosion; moreover, said rubber conductible sheet (70) and the foundation (81) of said bottom cover (80) form a tight pressing contact with the foundation (81) of said bottom cover (80) to seal mist or sweat from getting into the central district of said bottom cover (80) so as to prevent said circuit board (30) from being damped and effecting its function.

3. The prior wireless heartbeat transmitter has disadvantages of distortion of monitored heartbeat signal due to mal-contact of connection between surface and surface, which is caused by user's movement and vibration. The present invention uses the pressing plate (65) to press and lock the front end (81) of said fixing band (60); consequently, the front end (81) of said fixing band (60), said pins (51) of said U-shaped contact rod (50), and the foundation of said bottom cover (80) form a steady and firm mechanism which will not loose from user's movement and vibration; therefore, the present invention has superior electrical connection and steady conductance path.

4. The positive electrode and the negative electrode at the bottom of said circuit board (30) are welded to said spiral springs (40); each of said spiral springs (40) respectively collars said contact positioning pins (52) of said two U-shaped contact rod (50) and is tightly inserted inside said spring detent groove (89) of said bottom cover (80); consequently, said spiral spring (40) will not suffer mal-contact caused by vibration, and said circuit board (30) and said U-shaped contact rod (50) have a superior electrical connect.

5. The rubber conductible sheet (70), and the circuit board (30) of the present invention form an excellent electrical connection and a superior steady conductance path mechanism, the wireless heartbeat transmitter of the present invention has a mechanism of water and mist proof and a mechanism of steady electrical connect, which effectively prevents distortion of monitored heartbeat signal.

What is claimed is:

1. A conductance path mechanism of a wireless heartbeat transmitter comprising an upper cover, a bottom cover provided with a front wall rib and a rear wall rib, a circuit board, two spiral springs, two U-shaped contact rods integrally molded on both left and right sides of said bottom cover, two fixing bands, two rubber conductible sheets and two pressing plate; and wherein said bottom cover further comprising a left wall rib and a right wall rib for connecting and strengthening said front wall rib and said rear wall rib, and two rib walls positioned around a contact positioning pin and located on both sides of a central district of said bottom cover to form a spring detent groove.

2. The conductance path mechanism according to claim 1, wherein said U-shaped contact rod has one horizontal portion totally inserted inside a foundation of said bottom cover, and has two vertical ends; and wherein one said vertical end is provided with three upward vertical pins protruding out of the foundation of said bottom cover and inserted into a rubber conductible sheet at the bottom of a fixing band to form a conductible, insert-connecting mechanism and the other vertical end of said U-shaped contact rods forms a contact positioning pin, which extend within said spring dent groove and places spiral springs on both sides of the bottom of said circuit board inside a collar of said contact positioning pin.

3. The conductance path mechanism according to claim 2, wherein lower sections of said spiral spring is tightly inserted inside said spring detent groove to make said spiral spring and said bottom cover form a tight and steady mechanism, and to make said spiral spring and said contact positioning pin form a superior electrical contact and an excellent conductance path.

4. The conductance path mechanism according to claim 3, further comprising a pressing plate sheet positioned at a front end surface of each fixing band to make said three upward vertical pins of said U-shaped contact rod completely inserted into the interior of said rubber conductible sheet.

* * * * *